United States Patent [19]

Modi et al.

[11] Patent Number: 4,816,593

[45] Date of Patent: Mar. 28, 1989

[54] HETEROCYCLIC ORGANOTIN COMPOUNDS

[75] Inventors: Pravin G. Modi; Timothy C. Ross; Paul R. Story, all of Columbia, S.C.

[73] Assignee: Cardinal Reserach & Development Co., Inc., Columbia, S.C.

[21] Appl. No.: 135,686

[22] Filed: Dec. 21, 1987

[51] Int. Cl.$^4$ .............................................. C07F 7/22
[52] U.S. Cl. ...................................... 556/89; 524/379; 524/382
[58] Field of Search .......................................... 556/89

[56] References Cited

U.S. PATENT DOCUMENTS

| | | | |
|---|---|---|---|
| 3,317,573 | 5/1967 | Stamm et al. | 556/89 |
| 3,709,918 | 1/1973 | Stapfer | 556/89 X |
| 3,828,007 | 8/1974 | Throckmorton et al. | 556/89 X |
| 3,856,840 | 12/1974 | O'Brien et al. | 556/89 X |
| 4,122,065 | 10/1978 | Bertozzi | 556/89 X |
| 4,254,017 | 3/1981 | Dworkin et al. | 556/89 |

Primary Examiner—Paul F. Shaver

[57] ABSTRACT

A new class of heterocyclic, mono-organotin compounds is described. The structure has a five membered ring containing tin, sulfur, and oxygen.

The compounds exhibit excellent characteristics for stabilizing polyvinyl chloride.

4 Claims, No Drawings

HETEROCYCLIC ORGANOTIN COMPOUNDS

This invention relates to a new organotin compound which contains:
(a) a tin atom;
(b) an organic group;
(c) a cyclic group containing tin, oxygen and sulfur; and
(d) a sulfur containing hydroxyalkyl wherein the sulfur is connected to tin.

These compounds are useful as heat and light stabilizers for polymeric, halogenated resins and, in particular, polyvinyl chloride (PVC).

Many organotin structures have been prepared and found to be useful in stabilizing polyvinyl chloride. Different compounds are used, depending upon the function of the PVC: flexible, rigid, food packaging, pipe, vessels, or structural. R represents an organic group.

| | |
|---|---|
| $RSn(SR)_3$ | U.S. Pat. No. 2,891,922 |
| $R_2Sn(O_2CR)_2$ | U.S. Pat. No. 2,344,002 |
| $R_2SnS$ | U.S. Pat. No. 2,746,946 |
| $(RSn)_2S$ ‖ S | U.S. Pat. No. 3,021,302 |
| $R_2Sn(SCH_2CO_2R)_2$ | U.S. Pat. No. 2,641,588 |
| $RO_2C(CH_2)_2SnCl_3$ | Offenlegungsschrift No. 2540210 |

Other U.S. Patents which display various related structures are:
U.S. Pat. No. 2,731,482
U.S. Pat. No. 2,731,484
U.S. Pat. No. 2,809,956
U.S. Pat. No. 2,883,363
U.S. Pat. No. 3,485,794
U.S. Pat. No. 3,565,931
U.S. Pat. No. 3,764,571
U.S. Pat. No. 4,062,881

The wide range of structures of organotins heretofore known as PVC stabilizers may each have a specific or many commercial disadvantages:
(a) Long chain hydrocarbons on the anionic group result in excess lubricity.
(b) Short chain hydrocarbons on the anionic may cause sticking to process equipment surfaces.
(c) Certain cyclic compounds reduce extrusion rates.
(d) Lower molecular weight compounds may have undesirable odors or excessive volatility.
(e) Esters may not have long term shelf life.
(f) Some anionic groups have thermal instability.

The present invention is a heretofore undescribed class of organotin compounds which are excellent polyvinyl chloride stabilizers and do not have the commercial problems outlined above. The descriptive structure is shown as follows:

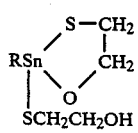

R is an organic group, preferably methyl, butyl, or octyl. The embodiment of this invention is disclosed in the following examples:

EXAMPLE #1

A three-knecked round bottom flask is fitted with a thermometer, agitator, a dropping funnel and a water bath. Twelve grams (0.30 mole) of sodium hydroxide and 175 g of water are charged into the flask and stirred until dissolution is complete and the temperature is below 30° C. At this point, 15.63 g (0.2 moles) of mercaptoethanol followed by the addition of 28.2 g (0.10 moles) of butyltin trichloride may be charged into the flask over a 15-minute period. The mixture may be stirred for 120 minutes maintaining temperature at 2°–30° C. and then isolated by filtration and dried at 25° C. and 760 mm Hg pressure, yielding 31.2 g (94.9% of theoretical yield).

| | Theoretical | Found |
|---|---|---|
| Molecular weight | 328.89 | 315 |
| % C | 29.20 | 29.60 |
| % H | 5.47 | 5.53 |
| % O | 9.73 | 9.85 |
| % S | 19.49 | 19.57 |
| % Sn | 36,09 | 35.70 |

Proton NMR data (300 MHz) indicates the structure to be:

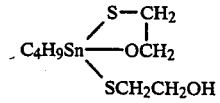

EXAMPLE #2

The apparatus and procedure of Example 1 may be used, substituting 33.8 g (0.10 mole) of octyltin trichloride for the butyltin trichloride to recover 36.9 g (96% of theoretical) of the octyltin heterocyclic compound. The product may have a tin asay within 2% of theoretical if dried completely.

EXAMPLE #3

The apparatus and procedure of Example 1 may be used, substituting 24.1 g (0.10 mole) of methyltin trichloride for butyltin trichloride to recover 27.1 g (93% of theoretical) of the methyltin heterocyclic compound. The product may have a tin assay within 5% of theoretical if dried completely.

EXAMPLE #4

A composition of this invention was evaluated as a PVC stabilizer in a Brabender button test apparatus with the following formulation commonly used for the manufacture of PVC pipe.

| Material | Parts (By Weight) |
|---|---|
| Shintech 950 Resin | 100.00 |
| Calcium Carbonate | 3.00 |
| Titanium Dioxide | 1.00 |
| XL-165 (American Hoechst Wax) | 1.00 |
| Calcium Stearate | 0.65 |
| AC-629A Oxidized Polyethylene (Allied) | 0.19 |
| Stabilizer | 0.40 |

The formulation was compared with a standard commercial PVC stabilizer identified as butyltin tris (isooctyl mercaptoacetate).

The results indicted a composition of this invention to be superior to the standard in respect to odor and heat degradation as shown below. The higher number indicates color formation, i.e., degradation.

|  | Rating (Time in Minutes) | | | |
|---|---|---|---|---|
| Invention Composition (butyl) | 1 | 2 | 5 | 10 |
| Butyltin tris I.O.M.A. | 1 | 2 | 6 | 11 |

What we claim is:

1. An organotin compound having the structure,

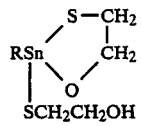

wherein R is an organic group containing one to eight carbon atoms.

2. An organotin compound described in claim one wherein R is butyl.

3. An organotin compound described in claim 1 wherein R is methyl.

4. An organotin compound described in claim 1 wherein R is octyl.

* * * * *